United States Patent [19]

Buendia et al.

[11] 4,072,755
[45] Feb. 7, 1978

[54] NOVEL CYCLOPENTANOIC ACID DERIVATIVES

[75] Inventors: Jean Buendia, Nogent sur Marne; Michel Vivat, Lagny-sur-Marne; Jeanine Schalbar, Suresnes, all of France

[73] Assignee: Roussel UCLAF, Paris, France

[21] Appl. No.: 717,049

[22] Filed: Aug. 24, 1976

[30] Foreign Application Priority Data

Aug. 29, 1975 France .................................. 75 26617

[51] Int. Cl.$^2$ ............................ A01N 9/24; C09F 5/00
[52] U.S. Cl. ...................................... 424/312; 260/404; 260/408; 260/410.9 R; 260/410.9 N; 260/413; 260/514 R; 260/514J; 260/514 K; 260/514 L; 424/308; 424/311; 424/317; 560/8; 560/76; 560/121; 560/129; 560/190; 560/231
[58] Field of Search ................. 260/410.9 P, 410.9 N, 260/410 P, 413 P, 468 D, 514 D, 514 R, 514 J, 514 K, 514 L, 468 R, 468 J, 468 K, 468 L, 488 R, 476 R, 404, 408; 424/308, 311, 312, 317

[56] References Cited

U.S. PATENT DOCUMENTS

| 3,880,906 | 4/1975 | Spraggins | 260/410 |
|---|---|---|---|
| 3,974,200 | 8/1976 | Schneider | 260/410.9 P |
| 3,993,674 | 11/1976 | Schaub et al. | 260/410.9 P |

OTHER PUBLICATIONS

Chemical Abstracts vol. 72: 72104d (1972).

Primary Examiner—Winston A. Douglas
Assistant Examiner—John F. Niebling
Attorney, Agent, or Firm—Hammond & Littell

[57] ABSTRACT

Novel cyclopentanoic acid derivatives of the formula

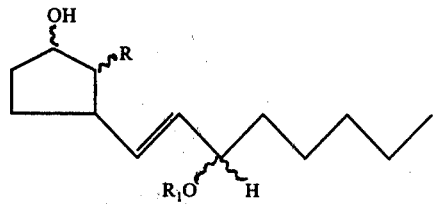

wherein R is selected from the group consisting of

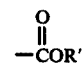

and —CH$_2$OH, R' is selected from the group consisting of hydrogen, alkyl of 1 to 4 carbon atoms and a non toxic, pharmaceutically acceptable cation and R$_1$ is selected from the group consisting of hydrogen, 2-tetrahydropyranyl, branched or straight chain, saturated or unsaturated alkyl of 1 to 4 carbon atoms and

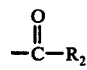

and R$_2$ is selected from the group consisting of straight or branched chain alkyl of 1 to 12 carbon atoms and phenyl with the alkyl and phenyl being optionally substituted with —COOA wherein A is selected from the group consisting of hydrogen, alkali metal, ammonium ion, ion of an organic amine, alkyl and haloalkyl of 1 to 7 alkyl carbon atoms with the proviso that R$_1$ is not hydrogen or 2-tetrahydropyranyl when R is a carboxylic group, and the OH and R groups on the ring and OR$_1$ group on the chain may be in either of the two possible positions about the carbon atom to which they are attached having analgesic, anti-inflammatory and smooth muscle relaxant activity.

15 Claims, No Drawings

NOVEL CYCLOPENTANOIC ACID DERIVATIVES

OBJECTS OF THE INVENTION

It is an object of the invention to provide the novel compounds of formula I and to provide a process for their preparation.

It is a further object of the invention to provide novel analgesic and anti-inflammatory compositions and to provide a novel method of relieving pain and inflammation in warm-blooded animals.

It is another object of the invention to provide novel smooth muscles relaxant compositions and to provide a novel method of relaxing smooth muscles in warm-blooded animals.

These and other objects and advantages of the invention will become obvious from the following detailed description.

THE INVENTION

The novel cyclopentanecarboxylic acid derivatives of the invention are comprised of compounds of the formula

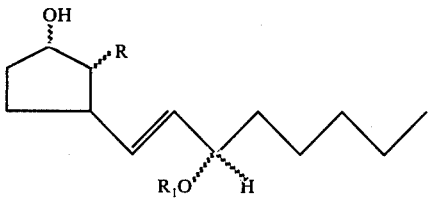

wherein R is selected from the group consisting of

and —CH$_2$OH, R' is selected from the group consisting of hydrogen, alkyl of 1 to 4 carbon atoms and a non toxic, pharmaceutically acceptable cation and R$_1$ is selected from the group consisting of hydrogen, 2-tetrahydropyranyl, branched or straight chain, saturated or unsaturated alkyl of 1 to 4 carbon atoms and

and R$_2$ is selected from the group consisting of straight or branched chain alkyl of 1 to 12 carbon atoms and phenyl with the alkyl and phenyl being optionally substituted with —COOA wherein A is selected from the group consisting of hydrogen, alkali metal, ammonium ion, ion of an organic amine, alkyl and haloalkyl of 1 to 7 alkyl carbon atoms with the proviso that R$_1$ is not hydrogen or 2-tetrahydropyranyl when R is a carboxylic group, and the OH and R groups on the ring and OR$_1$ group on the chain may be in either of the two possible positions about the carbon atom to which they are attached.

Among the R substituents are the free carboxyl group or its salts of lithium, sodium, potassium, calcium, magnesium or ammonium or salts with an organic amine base and esters thereof such as methoxycarbonyl, ethoxycarbonyl, propoxycarbonyl, isopropoxycarbonyl, butoxycarbonyl, isobutoxycarbonyl and tert.-butoxycarbonyl. Examples of R$_1$ are hydrogen, methyl, ethyl, acetyl, propionyl, hexanoyl, octanoyl, decanoyl, dodecanoyl, succinoyl, benzoyl and 2-carboxybenzoyl.

Among the preferred compounds of formula I are those wherein R is hydroxymethyl or alkoxycarbonyl of 1 to 3 alkoxy carbon atoms and R$_1$ is hydrogen, methyl or —COR$_2$ wherein R$_2$ is alkyl of 1 to 9 carbon atoms optionally substituted with COOA and A is hydrogen, or an alkali metal or R$_2$ is phenyl substituted with —COOH with the proviso that R$_1$ is not hydrogen when R is a carboxylic radical.

Specific preferred compounds of formula I are (1RS, 2SR, 5RS, 3'SR) (1'E) 2,3'-dihydroxy-5-(1'-octenyl)-cyclopentane methanol, ethyl (1RS, 2SR, 5RS, 3'SR) (1'E) 2-hydroxy-5-(3'-α-hemiphthaloyloxy-1'-octenyl)-cyclopentanecarboxylate, ethyl (1RS, 2SR, 5RS, 3'SR) (1'E) 2-hydroxy-5-(3'-decanoyloxy-1'-octenyl)-cyclopentanecarboxylate, ethyl (1RS, 2SR, 5RS, 3'SR) (1'E) 2-hydroxy-5-(3'-methoxy-1'-octenyl)-cyclopentanecarboxylate, ethyl (1RS, 2RS, 5RS, 3'SR) (1'E) 2-hydroxy-5-(3'-decanoyloxy-1'-octenyl)-cyclopentanecarboxylate and ethyl (1RS, 2SR, 5RS, 3'SR) (1'E) 2-hydroxy-5-(3'-hemisuccinyloxy-1'-octenyl)-cyclopentanecarboxylate.

The process of the invention for the preparation of compounds of formula I comprises either reacting a compound of the formula

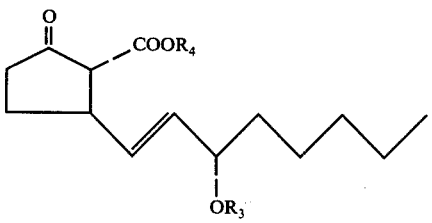

wherein R$_3$ is hydrogen or 2-tetrahydropyranyl and R$_4$ is alkyl of 1 to 4 carbon atoms with an alkali metal hydride at reflux in an organic solvent to obtain a compound of the formula

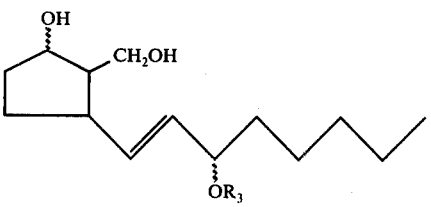

or reacting a compound of formula II wherein R$_3$ is hydrogen with an acid of the formula

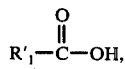

its acid chloride or anhydride of the formula

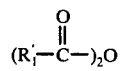

wherein R$_1$' is straight or branched alkyl of 1 to 12 carbon atoms or phenyl, both optionally substituted with —COOA' wherein A' is alkyl or haloalkyl of 1 to 7 carbon atoms to obtain a compound of the formula

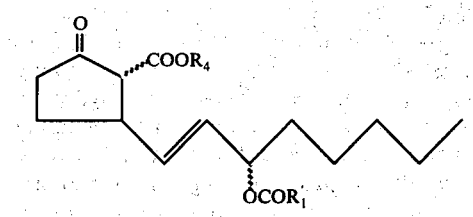

which is then reacted with a reducing agent to obtain a compound of the formula

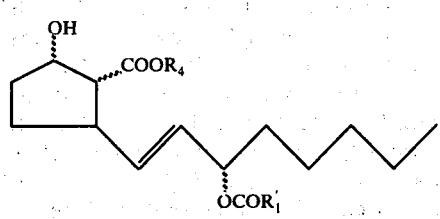

The compounds of formula Ib when $R_1'$ is alkyl or phenyl substituted with —COOA' and A' is haloalkyl may be treated with a reducing agent to obtain a compound of the formula

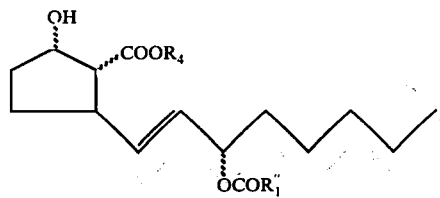

wherein $R_1''$ is alkyl or phenyl substituted with a free carboxylic acid group which may be salified by reaction with an alkaline base.

A compound of formula II wherein $R_3$ is hydrogen may also be reacted with diazomethane to obtain a compound of the formula

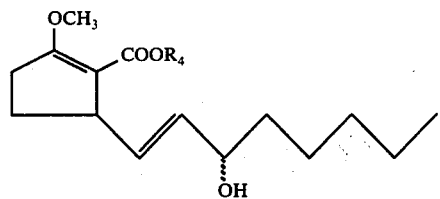

and the latter is reacted with an alkylation agent of the formula $R_3'$ X in an alkaline medium wherein $R_3'$ is branched or straight chain alkyl of 1 to 4 carbon atoms and X is a halogen to obtain a compound of the formula

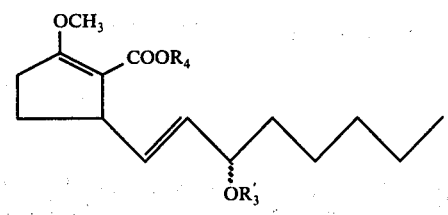

and the latter is treated with an acid to obtain a compound of the formula

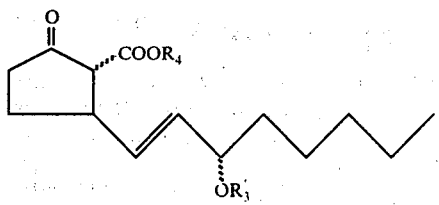

and the latter is treated with a reducing agent under mild conditions to obtain a compound of the formula

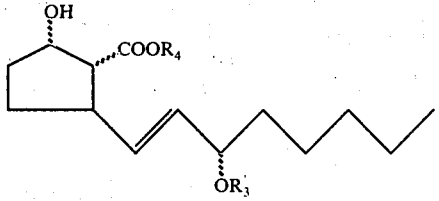

The compounds of formula Ib, Ic and Id may further be treated with an alkaline agent to form the corresponding free acid where $R_4$ is hydrogen which may be salified or esterified by the usual methods.

In a preferred mode of the process of the invention, the alkali metal hydride for reacting with the compound of formula II is sodium borohydride in a refluxing alkanol but also useful are potassium borohydride or lithium aluminum hydride in an inert organic solvent.

The compound of formula II may also be reacted with an acid chloride to obtain a compound of formula IV and to obtain good yields, a hydrochloric acid acceptor such as an alkali metal carbonate or bicarbonate or tertiary organic base such as triethylamine, picoline or pyridine is used.

The reducing agent used to treat the compound of formula IV is preferably sodium borohydride but equally useful is potassium borohydride or lithium aluminum hydride. The reducing agent used to change compound of Ib to a compound of Ic is a selective hydrogenolysis agent such as zinc in acetic acid.

The compound of formula V is treated with an alkyl iodide preferably but equally useful are an alkyl bromide or alkyl tosylate and the reaction is effected in the presence of an alkaline agent such as sodium hydride although other agents such as sodium amide or an alkali metal alcoholate like sodium tert.-butylate are equally useful.

The acid used to treat the compound of formula VI is preferably dilute hydrochloric acid in ethanol but equally useful are other dilute acids such as sulfuric acid or acetic acid in an inert organic solvent. The reducing agent to treat the compound of formula VII is preferably an alkali metal borohydride such as potassium borohydride or sodium borohydride at low temperatures but also useful are other alkali metal hydrides such as lithium aluminum hydride at a temperature below 0° C.

The alkaline agent used to treat compounds of formula Ib, Ic or Id to form the corresponding free acids may preferably be sodium hydroxide or potassium hydroxide but equally useful are barium hydroxide, lithium hydroxide or sodium or potassium bicarbonate and to obtain the esters, the corresponding alcohol is reacted with the acid in the presence of an acid agent to obtain the desired ester. The esters obtained in the process of the invention may be also transesterified with the appropriate alcohol.

The compounds of formula I wherein R' is hydrogen may be salified by known methods such as reacting the free acid with a mineral base such as sodium or potassium hydroxide or an organic base such as triethylamine. The reaction is preferably effected in at least one solvent such as water, ether, ethanol or acetone. The compounds of formula I occur in diverse configurations with respect to the carbon atoms to which the substituents are attached and the mixtures of the compounds formed in each instance may be separated by the known physical methods, particularly chromatography. The compounds of formula I may exist in the racemic form or as optically active isomers which are separated in the usual fashion. For example, the acids may be resolved by formation of salts with optically active bases.

The novel pharmacological compositions of the invention are comprised of at least one compound of formula I and an inert pharmaceutical carrier. The compositions may be in the form of tablets, dragees, gelules, granules, suppositories, injectable solutions or suspensions, pomades, creams, gels and aerosol preparation made in a known manner.

Examples of suitable excipients for the compositions are talc, arabic gum, lactose, starch, magnesium stearate, cacao butter, aqueous or non-aqueous vehicles, fatty bodies of animal or vegetable origin, paraffinic derivatives, glycols, preservatives and diverse wetting agents, emulsifiers or dispersants.

The compositions of the invention possess an antagonistic activity to prostaglandins as well as an antibiosynthesis action to prostaglandins. They are particularly endowed with analgesic, anti-inflammatory and smooth muscle relaxant properties. The compositions are therefore useful for the treatment of conditions caused by hypersecretion of prostaglandins or to prevent these conditions. They are also useful in the treatment of pain affecting smooth muscles, of acute or chronic pain, of inflammation of rhumatismic affections or of the skin and eyes (uveites) of hyperthemia expressed as a defense reaction. The compositions are also useful for the treatment of conditions resulting from hyperactivity of certain smooth muscles such as vascular conditions (diabetic retinopathy and cerebral constrictions), of bronchoconstriction (asthma and allergies), intestinal hypermotility, dysmenorrhea, of abortion dangers and of premature delivery.

The novel method of the invention for relieving pain nd inflammation in warm-blooded animals, including humans, comprises administering to warm-blooded animals an effective amount of at least one compound of formula I. The compounds may be administered orally, rectally, parenterally or locally by application to the skin or the mucous membranes and the usual useful dose is 0.4 to 40 mg/kg depending on the method of administrations.

The novel method of the invention for relaxing smooth muscles in warm-blooded animals comprises administering to warm-blooded animals an effective amount of at least one compound of formula I. The compounds may be administered orally, rectally, parenterally or locally by application to the skin or the mucous membranes and the usual useful dose is 0.4 to 40 mg/kg depending on the method of administrations.

In the following examples there are described several preferred embodiments to illustrate the invention. However, it should be understood that the invention is not intended to be limited to the specific emboidments.

EXAMPLE 1

(1RS, 2SR, 5RS, 3'SR) (1'E) 2,3,'-dihydroxy-5-(1'-octenyl)-cyclopentanemethanol

A mixture of 1 g of ethyl 3'(3'-hydroxy trans 1'-octenyl)-cyclopentane-2-carboxylate, 30 ml of ethanol containing 10% water and 1 g of sodium borohydride was refluxed for 3 hours and was then poured into water. The mixture was extracted with methylene chloride and the organic extracts were washed with dilute sodium hydroxide, dried and evaporated to dryness. The residue was chromatographed over silica gel and was eluted with a 60-20-15 chloroform-ethyl acetate-isopropanol mixture to obtain 140 mg of the α-OH isomer and 80 mg of the β-OH isomer of (1RS, 2SR, 5RS, 3'SR) (1'E) 2,3'-dihydroxy-5-(1'-octenyl)-cyclopentane methanol with a Rf = 0.37 and 0.32, respectively (silica gel - chloroform-ethyl acetate-isopropanol mixture).

EXAMPLE 2 ethyl (1RS, 2SR, 5RS, 3'SR) (1'E) 2-hydroxy-5-(3'-α-trichloroethylphthaloyloxy-1'-octenyl)-cyclopentanecarboxylate and ethyl (1RS, 2RS, 5RS, 3'SR) (1'E) 2-hydroxy-5-(3'-α-trichloroethylphthaloyloxy-1'-octenyl)-cyclopentanecarboxylate STEP A: Ethyl (1RS, 5RS, 3'SR) (1'E) 2-oxo-5-(3'-α-trichloroethylphthaloyloxy-1'-octenyl)-cyclopentanecarboxylate A mixture of 29.6 g of phthalic acid anhydride, 21 ml of trichloroethanol and 50 ml of pyridine was refluxed for 2 hours and was then poured into a mixture of 300 ml of ice water and 63 ml of hydrochloric acid. The mixture was extracted with methylene chloride and the organic extracts were washed with water and extracted with sodium bicarbonate solution. The aqueous phase ws acidified and was extracted with methylene chloride. The organic extracts were dried and the solution was concentrated and iced and was then vacuum filtered to obtain 29 g of crystalline trichloroethyl hemiphthalate with a melting point of 118° C.

A solution of 4.55 g of the said product in 18 ml of thionyl chloride was refluxed for 30 minutes and was then concentrated to dryness. The resulting acid chloride was dissolved in 13.5 ml of methylene chloride and the resulting solution was added over an hour to a mixture of 2.16 g of ethyl 3-(3'-α-hydroxy trans 1'-octenyl)-cyclopentane-2 -carboxylate, 13.5 ml of methylene chloride and 4.55 ml of pyridine. The mixture was stirred for an hour and was then poured into water. The mixture was extracted with methylene chloride and the organic extracts were washed with dilute hycrochloric acid, with water and with aqueous sodium bicarbonate, was dried and evaporated to dryness. The residue was chromatographed over silica gel and was eluted with a 75-25 cyclohexane-ethyl acetate mixture to obtain 2.7 g of ethyl (1RS, 5RS, 3'SR, 1'E) 2-oxo-5-(3'-α-trichloroethylphthaloyloxy-1'-octenyl)-cyclopentanecarboxylate with a Rf = 0.33 (silica gel-methylene chloride).

STEP B: ethyl (1RS, 2SR, 5RS, 3'SR) (1'E) 2-hydroxy-5-(3'-α-trichloroethylphthaloyloxy-1'-octenyl)-cyclopentanecarboxylate and ethyl (1RS, 2RS, 5RS, 3'SR) (1'E) 2-hydroxy-5-(3'-α-trichloroethylphthaloyloxy-1'-octenyl)-cyclopentanecarboxylate 285 mg of sodium borohydride were slowly added at 5° C to a solution of 4 g of the product of Step A in 120 ml of ethanol and 12 ml of water and the solution was stirred at 5° C for 45 minutes. The mixture was poured in aqueous sodium chloride and the mixture was extracted with ether. The organic extracts were washed with aqueous sodium chloride, dried and evaporated to dryness. The residue was chromatographed over silica gel and was eluted with a 97.5-2.5 methylene chloride-isopropyl ether mixture to obtain 1.9 g of the 2-α-OH isomer and 1.1 g of 2-β-OH isomer with an Rf = 0.57 and 0.54, respectively (silica gel -1-1 cyclohexane-ethyl acetate mixture).

EXAMPLE 3 ethyl (1RS, 2SR, 5RS, 3'SR) (1'E) 2-hydroxy-5-(3'-α-hemiphthaloyloxy-1'-octenyl)-cyclopentanecarboxylate 2.6 g of zinc were added at 20° C to a solution of 1.3 g of the α-isomer of Step B of Example 2 in 10.5 ml of acetic acid containing 20% water and the mixture was stirred for 2 hours and was then filtered. The filtrate was poured into water and the mixture was extracted with methylene chloride. The organic phase was washed with water, dried and evaporated to dryness. The residue was chromatographed over silica gel and was eluted with a 98.5-1.5 isopropyl ether-acetic acid mixture to obtain 540 mg of ethyl (1RS, 2SR, 5RS, 3'SR) 1'E) 2-hydroxy-5-(3'-α- hemiphthaloyloxy-1'-octenyl)-cyclopentanecarboxylate with an Rf = 0.17 (silica gel - 98-2 isopropyl ether-acetic acid).

EXAMPLE 4 sodium salt of ethyl (1RS, 2RS, 5RS, 3'SR) (1'E) 2-hydroxy-5-(3'-α-hemiphthaloyloxy-1'-octenyl)-cyclopentanecarboxylate Using the procedure of Example 3, the β—OH isomer of Step B of Example 2 was reacted and the resulting product was salified with sodium hydroxide or dilute sodium bicarbonate to obtain the sodium salt of ethyl (1RS, 2SR, 5RS, 3'SR) (1'E) 2-hydroxy-5-(3'-α-hemiphthaloyloxy-1'-octenyl)-cyclopentanecarboxylate.

EXAMPLE 5

Ethyl (1RS, 2RS, 5RS, 3'SR) (1'E) 2-hydroxy-5-(3'-decanoyloxy-1'-octenyl)-cyclopentanecarboxylate and ethyl (1RS, 2SR, 5RS, 3'SR) (1'E) 2-hydroxy-5-(3'-decanoyloxy-1'-octenyl)-cyclopentanecarboxylate.

Step A: ethyl (1RS, 5RS, 3'SR) (1'E) 2-oxo-5-(3'-decanoyloxy-1'-octenyl)-cyclopentanecarboxylate.

A mixture of 0.5 ml of thionyl chloride, 934 mg of capric acid and 4 ml of benzene was refluxed for 2 hours and then was evaporated to dryness to obtain capric acid chloride. The raw acid chloride was taken up in 5 ml of benzene and 1 ml of pyridine was added thereto. Then, a solution of 728 mg of ethyl 3'-(3'-α-hydroxy trans-1'-octenyl)-cyclopentane-2-carboxylate in 5 ml of benzene was slowly added to the mixture and after the addition of 66 mg of 4-dimethylaminopyridine, the mixture was stirred for 17 hours at 20° C. The mixture was poured into 1N hydrochloric acid and the mixture was extracted with ether. The ether extracts were washed with water, and aqueous sodium bicarbonate solution, dried and evaporated to dryness. The residue was chromatographed over silica gel and was eluted with an 8-2 cyclohexane-ethyl acetate mixture containing 0.1% of triethylamine to obtain 710 mg of ethyl (1RS, 5RS, 3'SR) (1'E) 2-oxo-5-(3'-decanoyloxy-1'-octenyl)-cyclopentanecarboxylate.

STEP B: ethyl (1RS, 2RS, 5RS, 3'SR) (1'E) 2-hydroxy-5-(3'-decanoyloxy-1'octenyl)-cyclopentanecarboxylate and ethyl (1RS, 2SR, 5RS, 3'SR) (1'E) 2-hydroxy-5-(3'-decanoyloxy-1'octenyl)-cyclopentanecarboxylate 243 mg of sodium borohydride were slowly added to a solution of 655 mg of the product of Step A in 10 ml of ethanol and 0.5 ml of water and the mixture was stirred at 0° C for 45 minutes. A few drops of acetone were added to the mixture which was then poured into an aqueous solution saturated with monosodium phosphate. The mixture was extracted with ether and the ether extracts were washed with water, dried and evaporated to dryness. The residue was chromatographed over silica gel and was eluted with an 8-2 cyclohexane-ethyl acetate mixture containing 0.1% of triethylamine to obtain 235 mg of ethyl (1RS, 2SR, 5RS, 3'SR) (1'E) 2-hydroxy-5-(3'-decanoyloxy-1'-octenyl)-cyclopentanecarboxylate [α-isomer] and 166 mg of ethyl (1RS, 2RS, 5RS, 3'SR) (1'E) 2-hydroxy-5-(3'-decanoyloxy-1'-octenyl)-cyclopentanecarboxylate [β-isomer].

| Analysis: | $C_{26}H_{46}O_5$ | |
|---|---|---|
| Calculated: | %C 71.19 | %H 10.57 |
| Found: α isomer: | 71.4 | 10.7 |
| β isomer: | 71.0 | 10.9 |

EXAMPLE 6 ethyl (1RS, 2SR, 5RS, 3'SR) (1'E) 2-hydroxy-5-(3'methoxy-1'-octenyl)-cyclopentanecarboxylate and ethyl (1RS, 2RS, 5RS, 3'SR) (1'E) 2-hydroxy-5-(3'-methoxy-1'-octenyl)-cyclopentanecarboxylate STEP A: ethyl (5RS, 3'SR) (1'E) 2-methoxy-5-(3'-hydroxy-1'-octenyl)-1-cyclopentenecarboxylate 300 ml of a solution of 15 g/liter of diazomethane in methylene chloride were added at 0° C to a solution of 7.01 g of ethyl 3-(3'-α-hydroxy trans 1-octenyl)-cyclopentane-2-carboxylate in 100 of methylene chloride and the mixture was stirred for 4 hours at 20° C. The mixture was evaporated to dryness and the residue was chromatographed over silica gel. Elution with a 4–6 cyclohexane-ethyl acetate mixture containing 0.1% of triethylamine yielded 6.3 g of ethyl (5RS, 3'SR) (1'E) 2-methoxy-5-(3'-hydroxy-1'-octenyl)-1-cyclopentenecarboxylate.

| Analysis: | $C_{17}H_{28}O_4$ | |
|---|---|---|
| Calculated: | %C 68.8 | %H 9.52 |
| Found: | 68.9 | 9.4 |

STEP B: ethyl (5RS, 3'SR) (1'E) 2-methoxy-5-(3'-methoxy-1'-octenyl)-1-cyclopentenecarboxylate 3 ml of hexamethylphosphotriamide, 724 mg of the product of Step A and 15 ml of ether were added at 20° C to a mixture of 460.8 mg of sodium hydride (50% mixture in mineral oil) and 15 ml of ether and the mixture was stirred for 20 minutes after which 0.6 ml of methyl iodide were added. After 20 hours at 20° C, the mixture was poured into water and the resulting mixture was extracted with ether. The ether extracts were washed with water, dried and evaporated to dryness.

The residue was chromatographed over silica gel and was eluted with a 6-4 cyclohexane-ethyl acetate mixture to obtain 615 mg of ethyl (5RS, 3'SR) (1'E) 2-methoxy-5-(3'-methoxy-1'-octenyl)-1-cyclopentenecarboxylate with a Rf = 0.4 (silica gel-1-1 cyclohexane-ethyl acetate mixture).

STEP C: ethyl (1RS, 5RS, 3'SR) (1'E) 2-oxo-5-(3'-methoxy-1'-octenyl)-cyclopentanecarboxylate A mixture of 615 mg of the product of Step B, 6.2 ml of ethanol and 0.6 and of 1N hydrochloric acid was stirred at 20° C for 16 hours and was then poured into water. The mixture was extracted with ethyl acetate and the organic extracts were washed with water, dried and evaporated to dryness. The residue was chromatographed over silica gel and was eluted with a 9-1 benzene-ethyl acetate mixture to obtain 500 mg of ethyl (1RS, 5RS, 3'SR) (1'E) 2-oxo-5-(3'-methoxy-1'-octenyl)-cyclopentanecarboxylate with an Rf = 0.34 (silica gel-9-1 benzene-ethyl acetate mixture).

STEP D: ethyl (1RS, 2SR, 5RS, 3'SR) (1'E) 2-hydroxy-5-(3'-methoxy-1'-octenyl)-cyclopentanecarboxylate and ethyl (1RS, 2RS, 5RS, 3'SR) (1'E) 2-hydroxy-5-(3'-methoxy-1'-octenyl)-cyclopentanecarboxylate 64 mg of sodium borohydride were added at −5° to 0° C to a mixture of 479 mg of the product of Step C, 16 ml of ethanol and 1.6 ml of water and the mixture was stirred for 1½ hours and was then poured into an aqueous solution saturated with monosodium phosphate. The mixture was extracted with methylene chloride and the organic extracts were washed with water, dried and evaporated to dryness. The residue was chromatographed over silica gel and was eluted with a 9-1 benzene-ethyl acetate mixture to obtain 210 mg of the α-OH isomer and 102 mg of the β-OH isomer of the above products with an Rf = 0.14 and 0.09 respectively (silica gel - 9-1 benzene-ethyl acetate mixture).

EXAMPLE 7 ethyl (1RS, 2SR, 5RS, 3'SR) (1'E) 2-hydroxy-5-(3'-β-trichloroethoxy succinyloxy-1'-octenyl)-cyclopentanecarboxylate STEP A: ethyl (1RS, 5RS, 3'SR) (1'E) 2-oxo-5-(3'-β-trichloroethoxy-succinyloxy-1'-octenyl)-cyclopentanecarboxylate A mixture of 500 mg of β-trichloroethyl hemisuccinate and 2 ml of thionyl chloride was heated at 80° C for 20 minutes and was then evaporated to dryness. The residue was taken up in methylene chloride and a mixture of 282 mg of ethyl 3-(3'-α-hydroxy trans 1'-octenyl)-cyclopentanone-2-carboxylate, 1.4 ml of pyridine and 2.8 ml of methylene chloride were added thereto. The mixture was stirred at 20° C for 20 minutes and 10 ml of water were added. The mixture was stirred for 15 minutes and was then extracted with methylene chloride. The extracts were washed with dilute hydrochloric acid, with water and with aqueous sodium bicarbonate, dried and evaporated to dryness. The residue was chromatographed with silica gel and was eluted with methylene chloride to obtain 350 mg of ethyl (1RS, 5RS, 3'SR) (1'E) 2-oxo-5-(3'-β-trichloroethoxy succinyloxy-1'-octenyl)-cyclopentanecarboxylate with an Rf = 0.5 (silica gel - 95-5 methylene chloride - isopropyl ether).

STEP B: ethyl (1RS, 2SR, 5RS, 3'SR) (1'E) 2-hydroxy-5-(3'-β-trichloroethoxy succinyloxy-1'-octenyl)-cyclopentanecarboxylate Using the procedure of Step B of Example 2, 1.33 g of the product of Step A were reacted to obtain a mixture of the α-OH and β-OH isomers of ethyl (1RS, 5RS, 3'SR) (1'E) 2-hydroxy-5-(3'-β-trichloroethoxy succinyloxy-1'-octenyl)-cyclopentanecarboxylate from which was isolated 380 mg of the α-OH isomer with a Rf = 0.4 (silica gel-8-2 methylene chloride - isopropyl ether).

EXAMPLE 8 ethyl (1RS, 2SR, 5RS, 3'SR) (1'E) 2-hydroxy-5-(3'hemisuccinyloxy-1'-octenyl)-cyclopentanecarboxylate 930 mg of powdered zinc were added over 5 minutes at 20° C to a mixture of 465 mg of the product of Step B of Example 7 and 3.5 ml of acetic acid containing 20% water and the mixture was stirred for 2 hours and was decanted. The organic phase was diluted with water and was extracted with ether. The ether phase was washed with aqueous sodium bicarbonate, acidified with dilute hydrochloric acid and extracted with ether. The ether extracts was washed with the water, dried and concentrated to dryness. The residue was chromatographed over silica gel and was eluted with a 79-20-1 chloroform-isopropyl ether-acetic acid mixture to obtain 220 mg of ethyl (1RS, 2SR, 5RS, 3'SR) (1'E) 2-hydroxy-5-(3'-hemisuccinyloxy-1'octenyl)-cyclopentanecarboxylate with an Rf = 0.3 (silica gel-above eluant).

| Analysis: | $C_{20}H_{32}O_7$ | |
|---|---|---|
| Calculated: | %C 62.48 | %H 8.39 |
| Found: | 62.6 | 8.6 |

PHARMACOLOGICAL DATA

The following compounds were used in the tests:
(1RS, 2SR, 5RS, 3'SR) (1'E) 2,3'-dihydroxy-5-(1'-octenyl)-cyclopentane methonol (product A);

ethyl (1RS, 2SR, 5RS, 3'SR) (1'E) 2-hydroxy-5-(3'-α-hemiphthaloyloxy-1'-octenyl)-cyclopentanecarboxylate (product B);

ethyl (1RS, 2SR, 5RS, 3'SR) (1'E) 2-hydroxy-5-(3'-decanoyloxy-1'-octenyl)-cyclopentanecarboxylate (product C);

ethyl (1RS, 2SR, 5RS, 3'SR) (1'E) 2-hydroxy-5-(3'methoxy-1'-octenyl)-cyclopentanecarboxylate (product D);

ethyl (1RS, 2RS, 5RS, 3'SR) (1'E) 2-hydroxy-5(3'-methoxy-1'-octenyl)-cyclopentanecarboxylate (product E);

ethyl (1RS, 2SR, 5RS, 3'SR) (1'E) 2-hydroxy-5-(3'-hemisuccinyloxy-1'-octenyl)-cyclopentanecarboxylate (product F); and ethyl (1RS, 2RS, 5RS, 3'SR) (1'E) 2-hydroxy-5-(3'-decanoyloxy-1'-octenyl)-cyclopentanecarboxylate (product G).

A. RELAXANT ACTIVITY ON THE GUINEA PIG ILEON

The relaxant effect of the test compounds was determined on guinea pig ileon using the following procedure. The terminal portion of the guinea pig ileon was removed and washed with Tyrode solution at 37° C. It was then suspended in a bath of oxygenated Tyrode liquid at 37° C and the contractions were registered on a collector attached to a Sanborn polygraph. The test product was added to bath of the organ with a low volume and the concentration which caused a suppression of spontaneous contractions and relaxed the organ causing a lowering of the line of the base was considered to be relaxant. The results are reported in Table I.

TABLE I

| Compound | Relaxant Activity in μg/ml |
|---|---|
| A | 20 |
| C | 20 |
| D | 5 |
| E | 10 |

B. ANALGESIC ACTIVITY-STRETCHING PROVOKED BY ACETIC ACID

The test procedure was that of Koster et al wherein an intraperitoneal injection of aqueous acetic acid in a concentration of 1% at a dose of 100 mg/kg caused in mice repeated movements of stretching and twisting which can persist for more than 6 hours. Analgesics prevent or lessen the syndrome. The test products were orally administered one half hour before the acetic acid injection and the mice were fasted from the day before the test. The stretching were counted for each mouse during a 15 minute observation period beginning right after the acetic acid injection and the analgesic effect was expressed as a percentage of protection with respect to the controls. The $DA_{50}$ dose which reduced the number of stretchings by 50% was determined for compound B and was found to be about 100 mg/kg.

C. INHIBITORY EFFECT AGAINST BIOSYNTHESIS OF PROSTAGLANDINS SYNTHESIS OF PROSTAGLANDINS STARTING WITH ARACHIDONIC ACID BY MEANS OF PROSTAGLANDIN SYNTHETASES OF LUNGS OF GUINEA PIGS.

This test used the procedure of Vane [Nature New Biology, Vol. 231 (1971), p. 232-235] wherein the lungs of adult guinea pigs (2 per series) were rapidly removed and washed with a modified, iced Bucher medium. The lung tissue was homogenized in a Turrax grinder in a minute and the homogenate was centrifuged for 20 minutes to 1200 g. The supernatant was used as a preparation of prostaglandin synthetases.

A solution of arachidonic acid in ethanol at a concentration of 10 mg/ml was diluted with a 0.2% aqueous sodium carbonate solution and was then diluted further with a modified Bucher medium to obtain a final acid concentration of 200 μg/ml. The biosynthesis inhibitors are put into aqueous or dilute alcohol (20% maximum) solutions. Tubes were prepared containing 1 ml of the prostaglandin synthetases preparation, 10 μg of arachidonic acid and 0.1 ml of inhibiting solution or, for the controls, an equal volume of water or dilute alcohol. The tubes were incubated with stirring for 30 minutes at 37° C in aerobic conditions and each test consisted of a tube containing a biosynthesis inhibitor, one biosynthesis control with incubated arachidonic acid and one control with non-incubated arachidonic acid. The latter control permitted a evaluation of amount of natural prostaglandins present in the ground lung and the results obtained with this control must therefore be taken away from the control of biosynthesis and from all the tests. The reactions were stopped by immension in boiling water until the proteins are coagulated. The dosage of "prostaglandin like" activity was effected biologically on the isolated rat colon suspended in Krebs liquid, mixed to augment the specificity, with antagonists to other contracturant mediators susceptible to interfere. The antagonists were mepyramine, scopolamine, methysergide, phenoxybenzamine and propanolol.

A comparison of the results registered in the presence or absence of a test product permitted the calculation of the percentage of biosynthesis inhibition. The $CI_{50}$ dose which inhibited by 50% the biosynthesis activity was graphically obtained by straight line representing the percent of inhibition with reference to the incubated controls against the log of the concentration in μg/ml and the results are reported in Table II.

TABLE II

| Product | $CI_{50}$ in $10^{-4}$ M |
|---|---|
| C | 1.37 |
| D | 4.36 |
| E | 6.71 |
| F | 1.23 |
| G | 1.13 |

Various modifications of the products and processes of the invention may be made without departing from the spirit or scope thereof and it is to be understood that the invention is to be limited only as defined in the appended claims.

We claim:

1. A compound of the formula

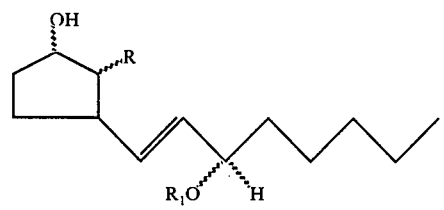

wherein R is

R' is selected from the group consisting of hydrogen, alkyl of 1 to 4 carbon atoms and a non-toxic, pharmaceutically acceptable cation and $R_1$ is selected from the group consisting of branched or straight chain, saturated or unsaturated alkyl of 1 to 4 carbon atoms and

and $R_2$ is selected from the group consisting of straight or branched chain alkyl of 1 to 12 carbon atoms and phenyl with the alkyl and phenyl being optionally substituted with —COOA wherein A is selected from the group consisting of hydrogen, alkali metal, ammonium ion, ion of an organic amine, alkyl and haloalkyl of 1 to 7 alkyl carbon atoms and the OH and R groups on the ring and $OR_1$ group on the chain may be in either of the two possible positions about the carbon atom to which they are attached.

2. A compound of claim 1 wherein R is alkoxycarbonyl of 1 to 3 alkoxy carbon atoms, $R_1$ is selected from the group consisting of hydrogen, methyl and —$COR_2$, $R_2$ is alkyl of 1 to 9 carbon atoms optionally substituted with COOA and A is selected from the group consisting of hydrogen and an alkali metal or R₂ is phenyl susbtituted with —COOH.

3. A compound of claim 1 which is ethyl (1RS, 2SR, 5RS, 3'SR) (1'E) 2-hydroxy-5-(3'-α-hemiphthaloyloxy-1'-octenyl)-cyclopentanecarboxylate.

4. A compound of claim 1 which is ethyl (1RS, 2SR, 5RS, 3'SR) (1'E) 2-hydroxy-5-(3'-decanoyloxy-1'-octenyl) -cyclopentanecarboxylate.

5. A compound of claim 1 which is ethyl (1RS, 2SR, 5RS, 3'SR) (1'E) 2-hydroxy-5-(3'-methoxy-1'-octenyl)-cyclopentanecarboxylate.

6. A compound of claim 1 which is ethyl (1RS, 2RS, 5RS, 3'SR) (1'E) 2-hydroxy-5-(3'-decanoyloxy-1'-octenyl)-cyclopentanecarboxylate.

7. A compound of claim 1 which is ethyl (1RS, 2SR, 5RS, 3'SR) (1'E) 2-hydroxy-5-(3'-hemisuccinyloxy-1'-octenyl)-cyclopentanecarboxylate.

8. An analgesic and anti-inflammatory composition comprising an effective amount of at least one compound of claim 1 and an inert pharmaceutical carrier.

9. A method of relieving pain and inflammation in warm-blooded animals comprising administering to warm-blooded animals an effective amount of at least one compound of claim 1.

10. The method of claim 9 wherein R is alkoxycarbonyl of 1 to 3 alkoxy carbon atoms, R₁ is selected from the group consisting of hydrogen, methyl and —COR₂, R₂ is alkyl of 1 to 9 carbon atoms optionally substituted with COOA and A is selected from the group consisting of hydrogen and alkali metal or R₂ is phenyl substituted with —COOH.

11. The method of claim 9 wherein the compound is ethyl (1RS, 2RS, 5RS, 3'SR) (1'E) 2-hydroxy-5-(3'-decanoyloxy-1'-octenyl)-cyclopentanecarboxylate.

12. A composition for relaxing smooth muscles comprising an effective amount of at least one compound of claim 1 and an inert pharmaceutical carrier.

13. A method of relaxing smooth muscles in warm-blooded animals comprising administering to warm-blooded animals an effective amount of at least one compound of claim 1.

14. The method of claim 13 wherein R is alkoxycarbonyl of 1 to 3 alkoxy carbon atoms, R₁ is selected from the group consisting of hydrogen, methyl and —COR₂, R₂ is alkyl of 1 to 9 carbon atoms optionally substituted with COOA and A is selected from the group consisting of hydrogen and an alkali metal or R₂ is pheyl substituted with —COOH.

15. The method of claim 13 wherein the compound is ethyl (1RS, 2RS, 5RS, 3'SR) (1'E) 2-hydroxy-5-(3'-decanoyloxy-1'-octenyl)-cyclopentanecarboxylate.

* * * * *